US008419608B2

(12) United States Patent
Feucht

(10) Patent No.: US 8,419,608 B2
(45) Date of Patent: Apr. 16, 2013

(54) APPARATUS FOR PRODUCING FIELDS FOR TREATMENT OF BODILY PARTS OF LIVING ORGANISMS FOR HEALING PURPOSES

(75) Inventor: Peter Feucht, Berlin (DE)

(73) Assignee: Mega-Wave-GmbH, Bad Worishofen (DE)

( * ) Notice: Subject to any disclaimer, the term of this patent is extended or adjusted under 35 U.S.C. 154(b) by 1602 days.

(21) Appl. No.: 11/904,114

(22) Filed: Sep. 26, 2007

(65) Prior Publication Data

US 2009/0082614 A1    Mar. 26, 2009

(51) Int. Cl.
*A61N 1/00* (2006.01)
(52) U.S. Cl.
USPC .................................................. 600/14

(58) Field of Classification Search ................. 600/9–15; 607/96
See application file for complete search history.

(56) References Cited

U.S. PATENT DOCUMENTS

2007/0179576 A1*  8/2007  Nagano et al. .................. 607/96

FOREIGN PATENT DOCUMENTS

EP            0 136 530 B1      6/1988

* cited by examiner

*Primary Examiner* — Christine Matthews
(74) *Attorney, Agent, or Firm* — Cort Flint

(57) ABSTRACT

In the process of generating high frequency magnetic fields for treating living organisms, an apparatus for limiting undesirable interference and disturbance that may be caused by electromagnetic radiation from said fields.

10 Claims, 2 Drawing Sheets

APPARATUS FOR PRODUCING FIELDS FOR TREATMENT OF BODILY PARTS OF LIVING ORGANISMS FOR HEALING PURPOSES

FIELD OF THE INVENTION

This invention relates to an apparatus for producing a high frequency for treatment of bodily parts of living organisms for healing purposes.

BACKGROUND

A known apparatus of the generic type for the generation of an electromagnetic field (hereinafter, "field") is disclosed by EP 0 136 530 B1. This known apparatus consists of a field producing means with a high frequency generator (hereinafter, "sender") having a device for the emission of a field of appropriate strength for treatment. Further, the known apparatus possesses at least one treatment capsule, which contains at least one magnetic coil electrically bound to the said sender. The sender is incorporated into the field producing apparatus by a cable and can be applied to the capsule for use directed to a bodily part of a living organism.

Briefly stated, the above cited field producing apparatus, for the achievement of therapeutic effects, allows the transport of high frequency energy at a carrier frequency in the range of 150 MHz, in order to exert minimal field strength treatment on athermous biological cells. In spite of the low field strength, which is in the range of about pA/m, it is possible, within the thereto associated capsule, or within a plurality of such capsules, that allowable official thresholds for emitted radio frequencies can be overstepped. The measured high frequency, disturbance levels can run to 20 to 40 dB above the permissible threshold values. Since, the range of concern is 150 MHz, transmission frequencies can be infringed upon, for example, mobile radio, GPS and like operations. On this account, maintaining officially specified threshold values is expressly desirable.

A shielding of a treatment room to achieve an observance of existing threshold values in the ambient neighborhood, would place a severe obstruction to the full use of a multi-value field producing unit. The application in non-specially shielded medicinal practices or in uses by patients at home would not be allowed. A considerable reduction of the field strength to allow high frequency treatments to operate within an officially approved level would, in great measure, destroy the medicinal practice of electromagnetic procedures.

Consequently, one object of the invention is to develop a novel electromagnetic apparatus in such a manner, that the high frequency outward radiation of disturbance range emitted from the sender is maintained under all conditions below a predetermined, non-critical value. Especially, this high frequency disturbance level is to be held within such a minimal range, that, for example, the specifications of governmental network agencies, in regard to degrees of interference frequencies are not infringed upon and a so-called "technical unobtrusiveness" can be maintained for the general practice of electromagnetic treatment.

SUMMARY OF THE INVENTION

The objects of the invention is achieved by a preferred embodiment which is a field producing apparatus for high frequency treatment of bodily parts of living organisms for the purpose of healing wherein the field producing apparatus includes a high frequency generator (sender) for the production of a high frequency current at a sender level, and the field producing apparatus includes an attached treatment capsule, which, at the least, possesses one magnetic coil for the generation of a high frequency field strength which is correlated to the actual field level of said sender, whereby the said capsule is in a treatment position of being, in an orderly manner, placed on a bodily part of a living organism for the high frequency treatment thereof or is in a state of load-free operation, when not in a functional position on a bodily part of a living organism and under such circumstances being devoid of damping of a high frequency field by living tissue whereby unacceptable high-frequencies can be radiated into the ambient environment, and wherein the field producing apparatus possesses a controller with a regulation or feature for the operational regulation of the high frequency level of the sender, the invention being characterized, in that an indicator is provided, which is enabled directly or indirectly to compare the value of the high frequency current from the sender to the treatment capsule and to set the same in a ratio, wherein this said ratio indicates the field strength values for the capsule in the treatment position and in the load-free position and can make known the values of the same, and in that in the case of a detected load-free situation the indicator issues a signal to shift, with which a switching of the field producing apparatus to a safety position is enacted, whereby the said field producing apparatus remains in the shutoff condition until the value of the sending level and therewith the thereto associated field strength, due to the action of a field-strength limitation feature, are reduced to a specified value, and in that even in a load-free situation, no unacceptable high frequency disturbing level can be emanated by the treatment capsule.

In accordance with the present invention, besides the known controller, a measurement apparatus is provided, by means of which, directly or indirectly, the strength of signal emitted by the sender to the magnetic field unit is compared with, and expressed as a ratio of the level of the field strength engendered by the said capsule. This ratio differentiates itself into a treatment (hereinafter "functional") position and a load-free position of the capsule. The said difference is captured in measurement technology, whereby a clear assessment for a treatment capsule in both its functional and its load-free positions is furnished. If a load-free position has been determined, then the indicator yields a "shift" signal. The action of the shift signal is to introduce a safety oriented operation in which the field producing apparatus is switched into a first alternative arrangement preventing a reconnection, so that under no circumstances can a disturbing output be emitted. In a second alternative, the sender level and therewith the field strength is toned down by means of a field strength limiting feature to such an extent, that in the load-free position, no unacceptable higher high frequency disturbance level can be broadcast into the ambient surroundings by the capsule.

An analysis of the problem of unacceptable levels of critical high frequency disturbances produced by the capsule indicates, that such disturbances are particularly found, when, with one or more magnetic coils, which act as magnetic sending antennae and during a load-free condition, these coils can broadcast high frequency disturbances. This load-free condition exists when the capsule is not being directed to a bodily part of a living organism, in simpler terms, directed. to a patient. Conversely to this situation, during patient centered applications, then a damping by the involved bodily tissue exists, whereby the high frequency emitted from the sender to the magnetic coil is predominately reduced and the therefrom resulting radiation load at the receiving magnetic coil is essentially at a minimum as is the disturbing frequency, even during the described load free operation.

In the case of a known field producing apparatus, which is in accord with the state of technology, a value adjustment facility sets the level of sender emission. By means of a predetermined level adjustment, a known therapeutic, predictable strength can be furnished by the capsule. However, this is the case only wherein the capsule emission is being damped by patient tissue. The involvement of this known system concerns a control without any feedback of the actually produced, magnetic coil to coil developed field strength. In a case wherein a carefully defined operation is being carried out and the field producing apparatus is applied to the patient in an orderly fashion, then this method of procedure leads to no unacceptably high frequency radiations. Conversely to this, in the load-free situation, wherein the direction of the field producing apparatus is not toward the patient, but is still at the same high level positioning of the sender, then an unacceptable radiation can be broadcast into the environment by a magnetic coil/magnetic coil ratio. In accordance with the present invention, the developed magnetic coil field strength is so restricted during a conventionally measured technologically critical, load-free, safety operation, that no, or at least minimal, high frequency levels are produced, whereby unacceptably high, high frequency broadcasts into the environment from the capsule are definitely excluded.

The indicator employed for the said purpose acts, in the described operation, as a sensing switch, which is dedicated to the treatment capsule and, so to speak, perceives whether or not the capsule is in a regulated and orderly application on bodily tissue or is in a state of load-free operation. For either, the indicating apparatus emits a thereto corresponding signal. The function of such a sensing switch is, from the standpoint of the invention, very simple, low in cost and operationally reliable for a direct or indirect comparison of the actual level of the sender with feedback on the field strength thereby caused on the capsule. In case the indicator perceives the information, that unacceptably high frequency levels are present, it is possible, the field producing apparatus is enabled to express an optical and/or acoustic warning and/or the said field producing apparatus can be shut off or the load on the sender is either shut down or else reduced to a non-critical level.

In a first alternative embodiment which includes the features of the preferred embodiment described above, a field strength sensor assigned to the treatment capsule is provided for the determination of the actual value of the field strength of the magnetic coil which said sensor is electrically connected to the indicator and, if required, is enabled to act as field strength source for the controller, and a field strength level sensor for the detection of the actual sender level is provided, which is connected to the indicator to enable a comparison between the assigned actual field strength and the load-free field strength, whereby, from the said result of the said comparison, the functional position or the load-free position of the capsule is determined. In addition, a field strength detector now serves the capsule for the determination of the field strength of the magnetic coil. This value is then input into the indicator and, if necessary, is to be considered as the source of the actual, field strength value for the controller. Also, a level sensor for the detection of the actual value at the sender is provided and is connected to the indicator. In this way, these two indicated values show a ratio of supplied current to the said actual field strengths, from which either the functional position or the load-free position of the capsule becomes evident.

The first alternate embodiment of the preferred embodiment may include an arrangement in which the field strength sensor is placed within the treatment capsule and thereby the electrical current and/or the electrical voltage of the magnetic coil is detected, whereby the rectified value, in linear or logarithmic terms, is directed through a signal wire to the controller, wherein the indicator is located. The field strength sensor is placed in the capsule, so that in this way, the electric current, and/or the electrical voltage of the magnetic coil can be inferred and the value is transmitted in a linear or a logarithmic form to be conducted through a signal line to the controller, and thus to the indicator.

A second alternative may include the above features of the first alternative and provide that in connection with the indicator a field strength sensor and a control sensor determine a direct and indirect value of the field strength in comparison to the sender level. This is aided by means of a directional coupler located on the high frequency output of the field producing apparatus to determine a standing wave measurement for the computation of a so-called standing wave ratio, whereby, with the aid of the said standing wave ratio determination may be made as to whether or not the capsule, in its properly ordered treatment position, has damped high frequency transmission by tissue absorption or is operating in a load-free condition. In case of the latter situation, the high frequency broadcast is not tissue-related-damped and in accord with the detected presence of a load-free condition, a specific control is sent to the weakener for the reduction of the sender level, or the field treatment itself is shut down.

This calls for a compact, reliable indicator. In connection with the said indicator, are to be found a field strength sensor and a control-sensor for a determination of the capsule field strength as compared to the output of the sender. This is aided by a directional coupler placed on the high frequency output port of the field producing apparatus to serve as a standing wave measurement device for obtaining a so-called standing wave ratio. This ratio enables a differentiation of the functional and load-free positions of the treatment capsule.

With the possession of the above determined standing wave ratio, it is possible to determine whether or not the capsule is being "tissue-damped" in an orderly therapeutic application position or is in a situation of load-free operation, wherein in the latter case, tissue damping is not available. After the determination of a load-free case, a weakening measure is activated to reduce the delivered field strength level or to shut down the resulting field itself.

The indicator is advantageously operated together with a controller. For this action, a controller possesses a compact regulation feature. To this regulation feature is input, the first actual field strength and second, the set-value field strength as determined by a set-value circuit. A predetermined, logarithmic value, as determined by a comparison of the said real and set values, is then issued as a adjustment signal. It is further possible, that control can be exercised on the sending level of the sender or, advantageously, on the thereby generated field strength of the magnetic coil.

In another alternative embodiment, the field producing apparatus of the preferred embodiment is to be basically so dimensioned, that by means of the set-value circuit, the field producing apparatus is to emit only such a maximum field strength, which, in the case of a capsule, is already situated on the bodily tissue of a living creature, and will not send any unwarranted high frequency emissions into the environmental atmosphere.

In yet another alternative of the preferred embodiment, the field strength limitation feature additionally possesses a start-up means, i.e., an initializing element, by means of which, in an initialization mode following the starting of the field producing apparatus, the sender is immediately controlled at such a small predetermined initial sending level, that, in neither of the two possible operational conditions, that is, in either the functional or the load-free position of the capsule, a high frequency disturbance level can be overstepped by the switching on of the said capsule. This is accomplished in that a defined low damped initial field level would be delivered at the initiating sender level while the capsule is on a bodily part of a living creature. In the case of a capsule, which is not so applied to tissue, in the initiation mode only, a definite higher load-free field strength could be allowed. The real value of the field strength is governed by a threshold control and a limiting value is set between the damped initial field strength and the described initial load-free field strength. Upon an overstepping of this threshold value in the initializing mode, an optical or an acoustic warning signal is produced, which advises the user in regard to the possible loss of the tissue placement of the treatment capsule. Upon an understepping of the threshold in the initializing mode, correspondingly involving a capsule properly addressed to a bodily tissue, then the initializing mode is ended and a release is made in favor of the controller.

It should be mentioned that by means of the existing initializing mode, a non-allowable higher high frequency disturbance level in the load-free condition is impossible from the earliest stage of operation. Without the initializing mode, it is possible that in a load-free state, after the switched-in inclusion of the field producing apparatus, primarily, an unacceptable higher high frequency disturbance level could be emitted, which then needs to be reduced.

Advantageously, a time oriented circuit may be included in any of the foregoing embodiments, with which the duration of a high frequency treatment time can be preset and, if necessary, the initializing mode can be activated.

The sender, the controller with its indicator and the regulation features and an assembly for the weakening of the sender's signal and, in some instances, an initializing element plus the operational and display units can all be contained in a unitized compact field producing apparatus. It is possible that one or more treatment capsules can be electrically bound to the field producing apparatus by means of a coaxial cable to allow convenient manipulation. If a plurality of treatment capsules are connected into one field producing apparatus, then each treatment capsule is obliged to have its own controller with an indicator.

Therapeutic action of a satisfactory order may be achieved, if, the high frequency oscillator produces a high frequency signal with a predetermined frequency in the range of 100 to 200 MHz, preferably about 150 MHz. Additionally it is possible that the high frequency signal can be modulated by a predetermined lower frequency and/or with a specified tact frequency.

DESCRIPTION OF THE DRAWINGS

The invention is described in greater detail with the aid of the attached drawings which are provided by way of illustration and not limitation. There is shown in.

DETAILED DESCRIPTION

Figure 1:
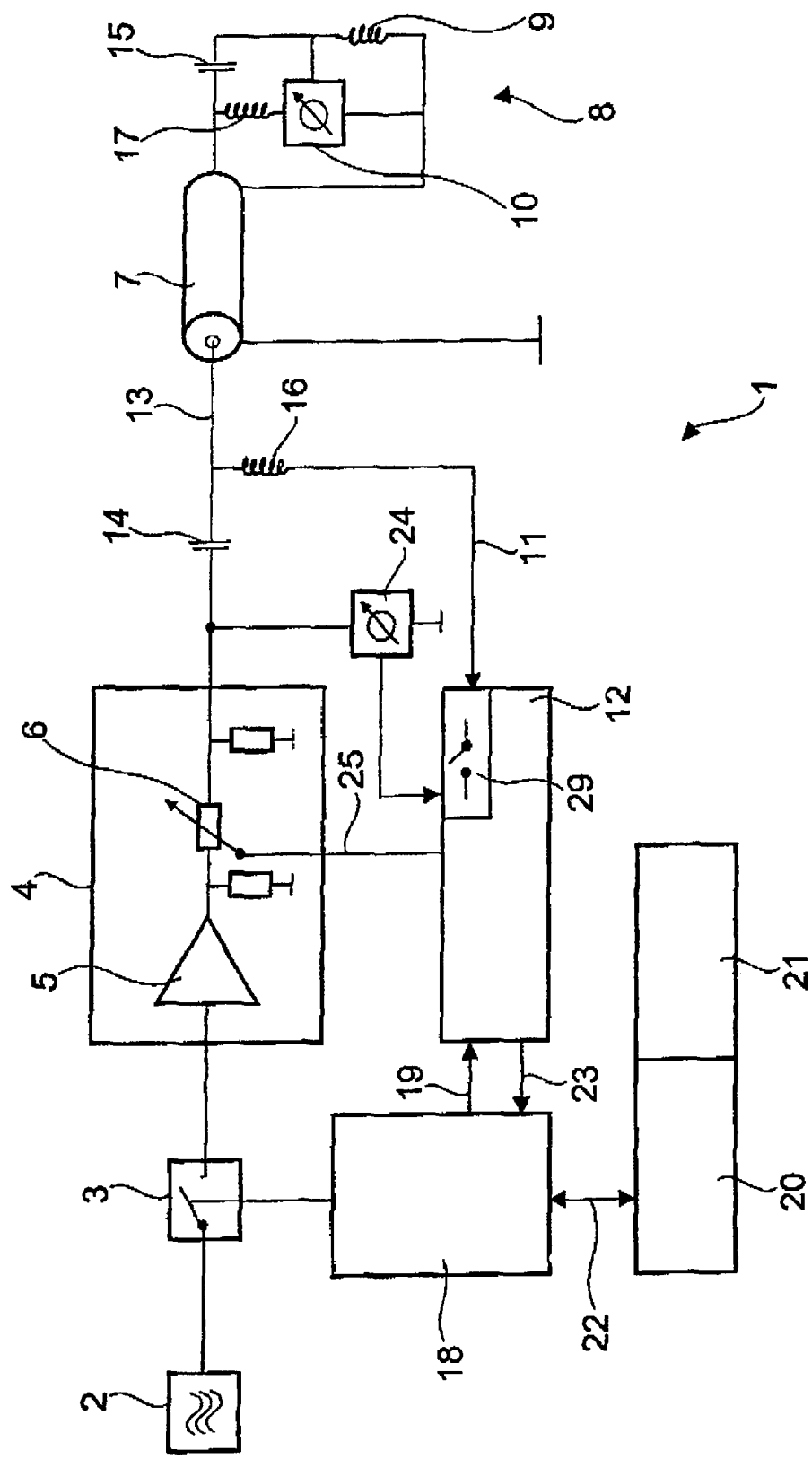
FIG. 1 a block circuit diagram of a first embodiment of a field producing apparatus, and in FIG. 2 a block circuit diagram of a second embodiment of a field producing apparatus.

The diagram of FIG. 1 concerns a first embodiment of a field producing apparatus 1, with a high frequency oscillator 2, which generates a carrier frequency of 150 MHz. Following the high frequency oscillator 2 is a switch 3 for the in and out switching of the field generation operation, whereby the said switch 3 can be coupled with a timer (not shown) and, schematically, can be made available for a modulation with lower frequencies and/or with a tact generator for wave packets for the enhancement of biological activity. A following sender weakening assembly 4 is connected to the switch 3 in which, schematically shown, is to be found a field weakener 6, which operates through a controllable, adjustable resistance. In brief, this device can be realized by the use of a "Voltage Controlled Gain Amplifier".

By means of a coaxial cable 7 a treatment capsule 8 is attached to the sender-weakening assembly 4. This is schematically shown in the circuit diagram, briefly noted as an object which can be directly placed upon a body part. Within the treatment capsule is to be found a magnetic coil 9 which serves as a magnetic antenna. Additionally the treatment capsule 8 has a field sensor 10, which determines the electrical current and/or the electrical voltage in the magnetic coil 9. This particular value is directed over a signal line 11 in a linear or a logarithmic manner to a controller 12. The controller 12 possesses an indicator 29 with a comparator as well as conventional feature for regulation.

The coaxial cable 7 (shown only in a partial view) is used in a threefold manner as follows: First, in that the high frequency line 13 from the sender weakener assembly 4 runs to the magnetic coil 9 through the condensers 14, 15. Second, the operational voltage source for the sensor 10 is supplied. Third, the signal line 11 from the field strength sensor 10 to the controller 12 for the determined actual field strength through the chokes 16, 17 is disconnected.

The actual field strength value is sent to the controller 12 through the signal wire 11, and at the same time, through wire 19 is sent from the microcontroller 18 a predetermined set value of the field strength. A service unit 20 and a display unit 21 are interconnected for data exchange purposes with the microcomputer by a signal line 22. Additionally, through the line 23 data from the controller 12, for example the said initiation mode, can be sent to the microcontroller. Further the level of the sending, in accord with the sender weakener assembly 4 is captured by the level sensor 24 and delivered to the controller through line 30. An exit gate of the controller 12 is connected to an adjustment line 25, which serves as a control line to the resistance type weakener 6, which is contained in the sender weakener assembly (4).

The illustrated arrangement has the following function: By means of the sender-weakener assembly 4 a downward modulated high frequency signal at 150 MHz is sent to the magnetic coil 9, i.e., to the treatment field producing coil. Simultaneously, the set field strength, which is in accord with medicinal requirements, is sent over the signal line 19 to the controller 12. The field strength which is generated in the magnetic coil 9 is picked up by the field strength sensor 10 and by way of the line 11 is sent back to the controller 12, particularly into the indicator 29 thereof. Additionally the sender level transmission from the level sensor 24 is picked up by the sender weakener assembly 4 as an actual sender level and sent likewise to the indicator 29. Each actual sender level actual value corresponds, within narrow limits, to a definite, assigned actual field strength, the respective strength whereof, is provided by the compact method of construction of the field producing apparatus. In the case of an orderly treatment capsule 8 already applied to a bodily part, it is possible that corresponding actual sender level values and thereto belonging actual field strengths can be empirically detected and, for example, be stored in a memory matrix. In the case of operation, interrogation is continually made with a comparator and shown on the indicator 29 as to whether or not this assignment is being carried out. If the answer is "YES", this is the direct determination that the field coil is properly in position for functioning on a bodily part. The indicator 29 releases the controller in the controller 12 to govern the field strength. At this point, a set value/real value comparison is made. In the case of a diversion, under some circumstances, under the inclusion of a control logarithm, which can be input into the microcomputer 18, a control signal for the weakener 6 is produced. In accord with the method of construction, it is not possible for an unacceptable higher high frequency disturbance signal to be emitted into the ambient environment.

If, in the course of operation of the indicator 29, a deviation from the above described procedure occurs, especially the appearance of an essentially higher field strength for a particular sender level actual value, than the assigned input actual field strength, then this is a positive indication of a load-free case, wherein damping is lacking, because of a treatment capsule which is not being applied to a bodily tissue. In this case, the normal regulation is not released. Instead of this said regulation, the actual value of the sender, and therewith the actual field strength is reduced by the resistance weakener 6 to a point lower than a non-critical disturbance of high frequency emissions for the environment. This would be true even in a case of a load-free situation. As an alternative, it is possible that the field producing apparatus can even be shut down. In such an event, start up could not be carried out until the treatment capsule had been properly repositioned on a bodily part.

The indicator 29 corresponds, in this respect, to a switch which is related to capsule placement on the bodily tissue. Accordingly, in a detected case of load-free operation, the said indicator has the capability of shifting from normal field strength regulation to another, non-critical method of operation.

Figure 2:
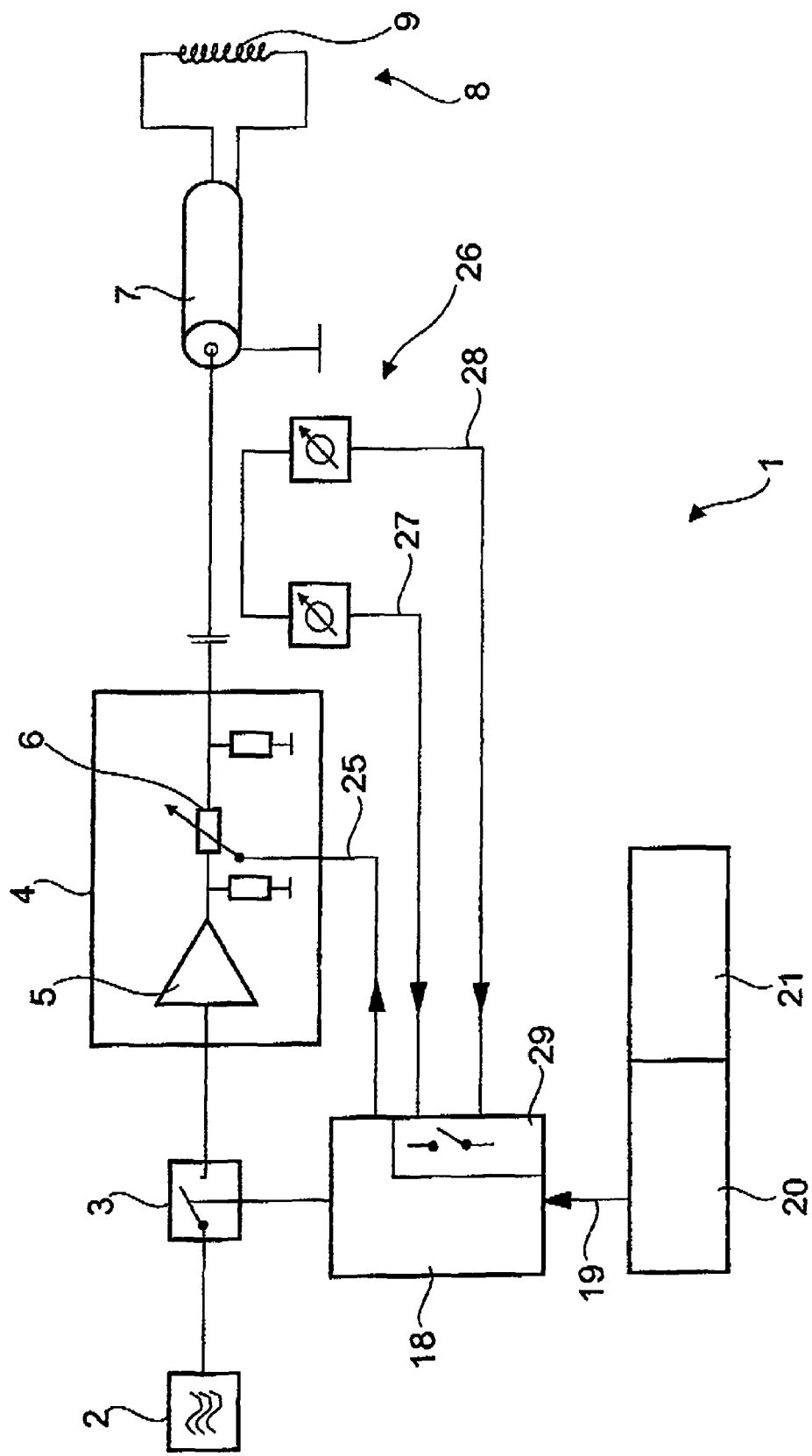

An alternative second embodiment of a field producing apparatus 1, as seen in FIG. 2, is arranged with some similarity to FIG. 1, so that the same reference numbers for the same components are repeated. Even in this second embodiment a high frequency oscillator 2, a switch 3, a sender weakener assembly 4 with a high frequency sender 5 and a resistance weakener 6 are present, as also are a coaxial cable 7 and a magnetic coil 9 to be used as a field producing coil. In addition a service unit 20 and a display apparatus 21 with a microcomputer 18 which possess the controller 18 and the indicator 29 are interconnected. A field strength set value is sent over the signal wire 19 directly to the microcomputer 18, from which, by means of an adjustment line 25 an adjustment signal is sent directly to the weakener 6. By means of a choke 26 and the indicator 29, the determination is made, as to in what manner the load sent from the sender weakener assembly 4 to the magnetic coil 9 is picked up. This said determination is as to whether or not a load-free case obtains, whereupon the so-called standing wave ratio is determined, and signals over the lines 27, 28 are sent to the microcomputer 18. If a case of load-free operation is detected, again in this situation as before, the normal regulation of the sending level is reduced and therewith the weakener 6 is correspondingly given control for the reduction of the field strength at the magnetic coil 9, so that no unacceptable high frequency disturbance levels in the ambient vicinity of the magnetic coil 9 and therewith at the treatment capsule have entered into a critical load free operation.

While a preferred embodiment of the invention has been described using specific terms, such description is for illustrative purposes only, and it is to be understood that changes and variations may be made without departing from the spirit or scope of the following claims.

What is claimed is:

1. A field producing apparatus for high frequency treatment of bodily parts of living organisms for the purpose of healing thereof comprising:
   a) a high frequency generator (sender) (5) for the production of a high frequency current at a sender level of the sender;
   b) a treatment capsule (8), which possesses at least one magnetic coil (9) for the generation of a high frequency field strength which is correlated to the sender level (5), said treatment capsule (8) having a first treatment position for orderly placement on a bodily part of a living organism for the high frequency treatment, and a second load-free position when not in a treatment position, the load free position being a load-free condition wherein an unacceptable high frequency disturbance can be radiated into an ambient environment;
   c) a controller (12) with a regulator for the operational regulation of said sender level;
   d) an indicator (29) sensing switch for comparing the sender level of said sender (5) to the field level of the treatment capsule (8) for establishing a set ratio value, wherein said ratio value indicates the field level for the capsule (8) in the treatment position and in the load-free position;
   e) said indicator (29), when detecting the load-free condition, issues a shifting signal for switching of the field producing apparatus (1) to a safety position so that said field producing apparatus (1) is placed in one of a shutoff condition or a reduced level condition until the ratio value of the sender level and field level are reduced to a specified ratio value so that no unacceptable high frequency disturbance level can be emanated by the treatment capsule under the load-free condition; and
   (f) a field level sensor (10; 26), assigned to the treatment capsule (8) for determining the field level of the magnetic coil (9), said field level sensor being electrically connected to the indicator (29) and further including a sender level sensor (24) for detection of the sender level which is connected to the indicator (29) to enable a comparison between the sender level and the field level so that, from the comparison, the load-free position of the capsule can be determined.

2. A field producing apparatus in accordance with claim 1, wherein the field level sensor (10) is included in the treatment capsule (8) and an electrical value of one of the electrical current and electrical voltage of the magnetic coil is detected and electrical value is directed through a signal wire (11) to the controller (12), in which the indicator (29) is located.

3. A field producing apparatus in accordance with claim 2, including a directional coupler (26) located on an output of the field producing apparatus to determine a standing wave measurement for computation of a standing wave ratio for determining whether the capsule (8) is in the treatment position and has a damped high frequency transmission by tissue absorption, or is in the load-free condition wherein the high frequency is not damped by high frequency transmission, and with the detection of a load-free condition, a specific control is sent to a level weakener which reduces the sender level.

4. A field producing apparatus in accordance with claim 3 including a micro controller (18) co-acting with said controller (12) to which the field level, as well as the sender level is delivered, said controller (12) generating an adjustment signal (25) based on a comparison of the field level and the sender level, and including a sender weakener assembly (4), containing a resistance weakener (6) to which the adjustment signal is delivered by indicator (29), so that, in a case of the field level being greater than the sender level, the adjustment signal will cause the sender level and field level to be reduced and, in a case of the field level being lower than the sender level, the resistance weakener will increase the field level.

5. A field producing apparatus according to claim 4 including a field level determinator for limiting the field level and preventing an unacceptable high frequency disturbance level during operation of the treatment capsule (8).

6. A field producing apparatus in accordance with claim 5, wherein the field level determinator includes an initialization mode wherein the sender level is controlled to deliver a low, predetermined, starting sender level following initial activation, either in the first treatment position or the load-free position of the capsule (8), so that a high frequency disturbance level during the initial activation can be prevented; and including a threshold means for indicating a threshold value bordering between the treatment position and the load-free position, and including an alarm that upon overstepping the threshold value, said alarm is activated to advise a service person in regard to a failure of a placement of the capsule on organic tissue and upon an understepping of the threshold value, the initial activation of the capsule placed on organic tissue is terminated, and the controller (12) is released from the initialization mode to begin normal operation.

7. A field producing apparatus, in accordance with claim 6, including a timer device for activation of start-up of the treatment so that the treatment may be automatically shut down following a specified duration of the treatment and restarted in the initialization mode.

8. A field producing apparatus in accordance with claim 7, wherein said micro controller has an indicator for controlling the treatment capsule for operation.

9. A field producing apparatus in accordance with claim 8, including a high frequency oscillator (2) for producing a high frequency signal at a predetermined value in the range of 100 to 200 MHz and including means for modulating the high frequency signal in response to one or both of a predetermined low-frequency and a predetermined high frequency.

10. A field producing apparatus in accordance with claim 9, wherein the predetermined value is about 150 MHz.

\* \* \* \* \*